(12) United States Patent
Hupfeld

(10) Patent No.: US 11,147,841 B2
(45) Date of Patent: Oct. 19, 2021

(54) ENHANCED OMEGA-3 FORMULATIONS

(71) Applicant: AKER BIOMARINE ANTARCTIC AS, Stamsund (NO)

(72) Inventor: Stefan Hupfeld, Kolbotn (NO)

(73) Assignee: AKER BIOMARINE ANTARCTIC AS, Stamsund (NO)

( * ) Notice: Subject to any disclaimer, the term of this patent is extended or adjusted under 35 U.S.C. 154(b) by 0 days.

(21) Appl. No.: 14/965,433

(22) Filed: Dec. 10, 2015

(65) Prior Publication Data
US 2016/0175366 A1    Jun. 23, 2016

Related U.S. Application Data

(60) Provisional application No. 62/094,364, filed on Dec. 19, 2014.

(51) Int. Cl.
| | | |
|---|---|---|
| *A61K 35/612* | (2015.01) | |
| *A23D 9/02* | (2006.01) | |
| *A23D 9/013* | (2006.01) | |
| *C11B 1/10* | (2006.01) | |
| *A23D 9/007* | (2006.01) | |
| *A61K 35/60* | (2006.01) | |
| *A61K 31/685* | (2006.01) | |
| *A61K 47/44* | (2017.01) | |
| *A61P 3/06* | (2006.01) | |
| *A61K 31/232* | (2006.01) | |
| *A61K 31/661* | (2006.01) | |

(52) U.S. Cl.
CPC ............ *A61K 35/612* (2013.01); *A23D 9/007* (2013.01); *A23D 9/013* (2013.01); *A23D 9/02* (2013.01); *A61K 31/232* (2013.01); *A61K 31/661* (2013.01); *A61K 31/685* (2013.01); *A61K 35/60* (2013.01); *A61K 47/44* (2013.01); *A61P 3/06* (2018.01); *C11B 1/10* (2013.01)

(58) Field of Classification Search
CPC .... A61K 35/612; A61K 35/60; A61K 31/685; A61K 47/44; A61K 31/232; A61K 31/661; A23D 9/02; A23D 9/13; A23D 9/007; C11B 1/10; A61P 3/06
See application file for complete search history.

(56) References Cited

U.S. PATENT DOCUMENTS 9,458,409 B2 * 10/2016 Hallaraker ........... A61K 31/683
2006/0128665 A1 6/2006 Leigh et al.
2008/0058286 A1 3/2008 Bruheim
2009/0074857 A1 3/2009 Dror et al.
2013/0095142 A1 4/2013 Shin
2014/0134228 A1 5/2014 Settineri
2014/0370115 A1 12/2014 Hoem et al.

FOREIGN PATENT DOCUMENTS

| CN | 102987382 A | 3/2013 |
|---|---|---|
| WO | 02/056709 | 7/2002 |
| WO | 2008/017957 | 2/2008 |
| WO | 2008/117062 | 10/2008 |
| WO | 2009/027692 | 3/2009 |
| WO | 2010/035013 | 4/2010 |
| WO | 2010/097701 | 9/2010 |
| WO | 2011/050474 | 5/2011 |
| WO | 2012/172411 | 12/2012 |
| WO | 2013/102792 | 7/2013 |
| WO | 2013/127727 | 9/2013 |
| WO | 2014/057362 | 4/2014 |
| WO | 2014/207571 | 12/2014 |
| WO | 2015/104401 | 7/2015 |

OTHER PUBLICATIONS

International Search Report, International Patent Application No. PCT/IB2015/002466, dated Mar. 30, 2016.
Batetta B et al. "Endocannabinoids may mediate the ability of (n-3) fatty acids to reduce ectopic fat and inflammatory mediators in obese Zucker rats." (2009) J Nutr 139(8):1495-1501.
Homan R et al. "Rapid separation and quantitation of combined neutral and polar lipid classes by high-performance liquid chromatography and evaporative light-scattering mass detection" (1998) J Chromatogr B Biomed Sci Appl 708:21-26.
Moreau et al. "The analysis of lipids via HPLC with a charged aerosol detector." (2006) Lipids 41:727-734.
Watanabe et al. "Effective Components in Cuttlefish Meal and Raw Krill for Improvement of Quality of Red Seabream Pagrus major Eggs" (1991) Nippon Suisan Gakkaishi 57:681-94.
Winther et al. "Elucidation of Phosphatidylcholine Composition in Krill Oil Extracted from Euphausia superba" (2011) Lipids 46:25-36.

\* cited by examiner

*Primary Examiner* — Sahar Javanmard
(74) *Attorney, Agent, or Firm* — Casimir Jones, S.C.; J. Mitchel Jones

(57) ABSTRACT

The present invention relates to enhanced omega-3 formulations, and in particular to formulations comprising a phospholipid fraction and a triglyceride fraction in combinations with agents that provide a formulation with improved viscosity and dispersion characteristics.

7 Claims, No Drawings

ENHANCED OMEGA-3 FORMULATIONS

CROSS-REFERENCE TO RELATED APPLICATIONS

This application claims the benefit U.S. Provisional Patent Application No. 62/094,364 filed Dec. 19, 2014, the contents of which is incorporated by reference in its entirety.

FIELD OF THE INVENTION

The present invention relates to enhanced omega-3 formulations, and in particular to formulations comprising a phospholipid fraction and a triglyceride fraction in combinations with agents that provide a formulation with improved viscosity and dispersion characteristics.

BACKGROUND OF THE INVENTION

Accumulating evidence indicates that long chain omega-3 fatty acids found in fish, docosahexaenoic acid (DHA) and eicosapentaenoic acid (EPA), decrease the risk of coronary heart disease (CHD) and ischemic heart disease. Large epidemiological studies, such as the Physicians' Health Study and the Nurses' Health Study, examined dietary and other lifestyle factors that influence health outcomes. The Physician's Health Study reported that consumption of one or more servings of fish per week was associated with a 52% lower risk of sudden cardiac disease compared to less than one fish meal per week. In another epidemiological study, the Nurses Health Study in America, it was found that consumption of five or more servings of fish per week was associated with 45% fewer cardiac deaths compared to consumption of one fish meal per month. Long chain omega-3 fatty acids are known to be a protective dietary factor for cardiovascular disease. EPA and DHA have been shown to lower triglyceride levels and act as anti-arrhythmic agents. The American Heart Association (AHA) performed comprehensive reviews of the data for fish and fish oil consumption and cardiovascular disease. The AHA report recommends that individuals with and without heart disease and elevated blood triglyceride levels consume fish or take a fish oil supplement. A report prepared in 2003 by The Third Task Force of European and Other Societies also recommends fish oil as a standard therapy for post-myocardial infarction management.

The level of triglycerides in blood is positively associated with an increase in CHD, as triglyceride levels increase so does the risk of CHD. Multiple factors influence the elevation of serum triglycerides throughout life with a major contributor being the diet. Both DHA and EPA, which are abundant in many marine seafood products, appear to support cardiovascular health and lower blood triglyceride levels. It is known that fish oil can reduce serum triglyceride levels by 20-50%, similar to the effects observed with medications such as statins, niacin and fibrates. The American Heart Association recommends that individuals without documented CHD consume two servings of fish (preferably fatty fish, please see Food products) per week. Patients with CHD should consume 1 gram of EPA and DHA per day preferably from fatty fish or in a supplemental form (if under the care of a physician). For those patients who need to lower triglyceride levels, the American Heart Association recommends 2-4 grams of EPA and DHA per day in supplemental form under a physician's care. A prescription form of EPA and DHA, Lovaza (formerly known as Omacor), is a good omega-3 fatty acid source available for people with high levels of blood triglycerides. Each Lovaza 1 gram capsule contains 465 mg EPA ethyl ester, 375 mg DHA ethyl ester, 80 mg of other omega-3 fatty acids, 30 mg of omega-6 fatty acids and 50 mg of antioxidants. It is prescribed as an adjunct to diet to reduce very high triglyceride levels in adult patients.

In medical research, omega-3 fatty acids are being investigated to determine whether they can effectively improve a wide range of disease states-among them, heart disease, diabetes, inflammation, depression, Alzheimer's and attention deficit disorder—making this group of nutrients an exciting and very active area of clinical research. Ensuring that omega-3 fatty acids are a part of the diet as recommended by dietary guidelines is a proper starting point to achieving better health; hence, a great opportunity exists in the potential for improving the human condition with omega-3 fatty acids.

In order to provide an effective dose of EPA and DHA, it is often necessary for a subject to ingest 2 to 4 capsules containing an omega-3 supplement. In order to reduce the number of capsules necessary, some omega-3 products are provided as omega-3 concentrates in the form of either triglyceride concentrates or ethyl ester concentrates that contain an enhanced content of EPA and DHA as compared to fish oil. However, when these products are combined with a lipid fraction comprising predominantly phospholipids, the resulting formulation displays problems including high viscosity, phase separation and poor dispersion characteristics.

SUMMARY OF THE INVENTION

The present invention relates to enhanced omega-3 formulations, and in particular to formulations comprising a phospholipid fraction and a triglyceride fraction in combinations with agents that provide a formulation with improved viscosity and dispersion characteristics.

In some embodiments, the present invention provides lipid formulations comprising: about 25 to 55% w/w of a first lipid fraction comprising from about 50%, 52%, 54%, or 56% to 100% w/w phospholipids derived from a marine source; about 40% to 70% w/w of a second lipid fraction comprising from about 70% to 100% triglycerides; and one or more additives selected from the group consisting of about 1% to 8% of an alcohol and about 1% to 20% of a surfactant and combinations thereof. In some embodiments, the first and second lipid fractions are extracted from different source materials. In some embodiments, the first and second lipid fractions are fractions that are separately extracted from the same source material. In some embodiments, the first lipid fraction is extracted from a marine source selected from the group consisting of krill, squid and herring.

In some embodiments, the first lipid fraction is extracted from a krill source material. In some embodiments, the lipid fraction is a krill lipid fraction comprising from about 50%, 52%, 54%, 56%, 60% or 70% to 100% phospholipids w/w, the phospholipids being further characterized in having a combined EPA and DHA content of from about 25% to 40% w/w of the krill lipid fraction.

In some embodiments, the krill lipid fraction comprises a mixture of phospholipid compounds of formula (I):

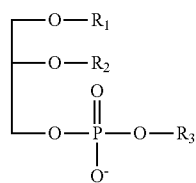

wherein:
R$_1$ and R$_2$ are each independently selected from a fatty acid moiety of formula —COC$_n$H$_m$, a fatty acid moiety of formula —CH$_2$C$_n$H$_m$, and —H;
R$_1$ and R$_2$ include omega-3 fatty acid moieties, such that at least 30% by weight of the phospholipid compounds is composed of omega-3 fatty acid moieties;
at least 90% by weight of total omega-3 fatty acid moieties are at position R$_2$;
R$_1$ and R$_2$ are not both —H in a phospholipid compound, and R$_1$ or R$_2$ is —H in less than 3% by weight of the compounds of formula (I);
R$_3$ is selected from —H, a choline moiety, an ethanolamine moiety, a N-acetylethanolamine moiety, an inositol moiety, and a serine moiety; and
R$_3$ is a choline moiety in at least 85% by number of the compounds of formula (I).
and wherein the krill phospholipid fraction also has one or more of the following properties:
(a) at least 50%, 52%, 54%, 56%, 60% or 70% by weight of the krill phospholipid fraction consists of phospholipid compounds of formula (I);
(b) the weight ratio of C16:0/C14:0 fatty acid moieties in the krill phospholipid fraction is between 10:1 and 18:1 and/or the weight ratio of C18:4 n-3/C18:3 n-3 fatty acid moieties is between 1:1 and 3:2;
(c) the krill phospholipid fraction includes less than 300 μg astaxanthins per gram of phospholipid;
(d) the krill phospholipid fraction comprises less than 0.01% by weight trimethylamine N-oxide;
(e) the krill phospholipid fraction comprises less than 0.01% by weight homarine;
(f) the krill phospholipid fraction includes less than 5% by weight water;
(g) the krill phospholipid fraction has less than about 0.03% by weight PUFA polymers
(h) the krill phospholipid fraction includes both phospholipids where R$_1$ is a fatty acid moiety of formula —COC$_n$H$_m$ and phospholipids where R$_1$ is a fatty acid moiety of formula —CH$_2$C$_n$H$_m$;
(i) the krill phospholipid fraction includes both phospholipids where R$_1$ is an omega-3 fatty acid moiety and phospholipids where R$_2$ is an omega-3 fatty acid moiety;
(j) the krill phospholipid fraction includes less than 5% by weight sphingomyelin;
(k) the krill phospholipid fraction is free from chloroform and hexane; and/or
(l) less than 0.9% by weight of phospholipids in the composition is formed of compounds where R$_1$ or R$_2$ is —H, or more than 1.1% by weight of phospholipids in the composition is formed of compounds where R$_1$ or R$_2$ is —H.

In some embodiments, the second lipid fraction is extracted from a marine source. In some embodiments, the marine source is selected from the group consisting of krill, squid, fish and marine algae. In some embodiments, the second lipid fraction is a triglyceride omega-3 concentrate. In some embodiments, the triglyceride omega-3 concentrate is a fish oil concentrate. In some embodiments, the triglyceride omega-3 concentrate is characterized in comprising a combined content of EPA and DHA of from about 45% to 80% w/w of the triglyceride omega-3 concentrate. In some embodiments, the triglyceride omega-3 concentrate is characterized in comprising a combined content of EPA and DHA of from about 60% to 80% w/w of the triglyceride omega-3 concentrate.

In some embodiments, the lipid formulation comprises a total EPA and DHA content of from about 350 mg to 700 mg per gram of the formulation. In some embodiments, the lipid formulation comprises a total EPA and DHA content of from about 400 mg to 600 mg per gram of the formulation. In some embodiments, the formulation comprises a total EPA and DHA content of from about 425 mg to 575 mg per gram of the formulation.

In some embodiments, the alcohol is a food grade alcohol. In some embodiments, the food grade ethanol is ethanol. In some embodiments, the lipid formulation comprises from about 0.5% to 4% w/w of the alcohol. In some embodiments, the lipid formulation comprises from about 1% to 3% w/w of the alcohol.

In some embodiments, the lipid formulations comprise from about 1% to 20% of the surfactant. In some embodiments, the lipid formulations comprise from about 5% to 15% of the surfactant. In some embodiments, the surfactant is selected from the group consisting of a polysorbate and a sorbitan ester. In some embodiments, the polysorbate is selected from the group consisting of Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), and Polysorbate 80 (Polyoxyethylene (20) sorbitan monooleate). In some embodiments, the sorbitan ester is selected from the group consisting of Sorbitan monolaurate, Sorbitan monopalmitate, Sorbitan monostearate, Sorbitan monooleate, Sorbitan sesquioleate, Sorbitan trioleate and Sorbitan isostearate. In some embodiments, the surfactant is not a free fatty acid. However, in other embodiments, the present invention contemplates use of free fatty acids as surfactants and thus the term "surfactant" as used herein includes free fatty acids, preferably from a source other than krill. In some embodiments, the free fatty acid surfactants are preferably enriched for EPA and/or DHA.

In some embodiments, the lipid formulation has a viscosity of from about 20 to 200 mPas at 30° C. In some embodiments, the lipid formulation has a viscosity of from about 50 to 150 mPas at 30° C.

In some embodiments, the lipid formulation is provided in a formulation selected from the group consisting of a capsule, a tablet, a liquid, a powder, an emulsion, a dietary supplement, a nutritional supplement, a beverage and a functional food.

In some embodiments, the present invention provides a lipid formulation comprising: about 25 to 55% w/w of a first lipid fraction comprising from about 60% to 100% w/w phospholipids derived from a marine source; and about 40% to 70% w/w of a second lipid fraction comprising from about 70% to 100% triglycerides, wherein the lipid formulation has a viscosity of from about 20 to 200 mPas at 30° C. In some embodiments, the lipid formulation has a viscosity of from about 50 to 150 mPas at 30° C.

In some embodiments, the present invention provides methods for reducing serum triglycerides, reducing serum cholesterol, reducing plaque formation, reducing platelet aggregation, treating atherosclerosis, improving cardiovascular health, reducing inflammation, treating coronary heart disease, treating depression, treating Alzheimer's disease, treating attention deficit disorder, and treating metabolic syndrome comprising administering a lipid formulation as described above to a subject in need thereof. In some embodiments, the lipid formulation is administered in a daily dose of from about 0.1 to about 3 grams. In some embodiments, the formulation is administered to a subject selected from the group consisting of humans, non-human primates, domestic raised or farmed animals, and companion animals.

In some embodiments, the present invention provides for the use of a lipid formulation as described above for reducing serum triglycerides, reducing serum cholesterol, reducing plaque formation, reducing platelet aggregation, treating atherosclerosis, improving cardiovascular health, reducing inflammation, treating coronary heart disease, treating depression, treating Alzheimer's disease, treating attention deficit disorder, and treating metabolic syndrome. In some embodiments, the formulation is administered in a daily dose of from about 0.1 to about 3 grams. In some embodiments, the formulation is administered to a subject selected from the group consisting of humans, non-human primates, domestic raised or farmed animals, and companion animals.

In some embodiments, the present invention provide methods for the manufacture of a blended lipid formulation comprising: combining a first lipid fraction comprising from about 60% to 100% w/w phospholipids derived from a marine source with a second lipid fraction comprising from about 70% to 100% triglycerides to provide a lipid mixture; and mixing said lipid mixture until the first lipid fraction dissolves in the second lipid fraction. In some embodiments, the methods further comprise the step of combining a surfactant with the first lipid fraction and the second lipid fractions so that the blended lipid formulation comprises from about 1% to 20% of the surfactant. In some embodiments, the second lipid fraction is blended with a surfactant prior to the combination with the first lipid fraction so that the blended lipid formulation comprises from about 1% to 20% of said surfactant. In some embodiments, the first lipid fraction is solubilized in an alcohol and the method further comprising the step of evaporating the alcohol in the lipid mixture after combination of the fractions to provide a blended lipid formulation comprising about 25 to 55% w/w of said first lipid fraction, about 40% to 70% w/w of said second lipid fraction and from about 1% to 8% w/w of said alcohol.

Definitions

As used herein, "phospholipid" refers to an organic compound having the following general structure:

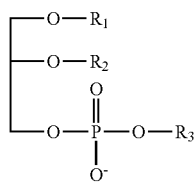

wherein R1 is a fatty acid residue or —H, R2 is a fatty acid residue or —H, and R3 is a —H or a phospholipid headgroup moiety such as a choline (HOCH$_2$CH$_2$N$^+$(CH$_3$)$_3$OH$^-$) moiety, ethanolamine (HOCH$_2$CH$_2$NH$_2$) moiety, serine moiety, inositol moiety such as cyclohexane polyol inositol, and derivatives thereof. Preferably, R1 and R2 cannot simultaneously be —H. When R3 is an —H, the compound is a diacylglycerophosphate, while when R3 is a nitrogen-containing compound, the compound is a phosphatide such as lecithin, cephalin, phosphatidyl serine or plasmalogen.

An "ether phospholipid" as used herein refers to a phospholipid having an ether bond at position 1 the glycerol backbone. Examples of ether phospholipids include, but are not limited to, alkylacylphosphatidylcholine (AAPC), lyso-alkylacylphosphatidylcholine (LAAPC), and alkylacylphosphatidylethanolamine (AAPE). A "non-ether phospholipid" is a phospholipid that does not have an ether bond at position 1 of the glycerol backbone.

As used herein, the term "long chain polyunsaturated fatty acid" refers to a fatty acid having 20 or more carbons and which is unsaturated at two or more bonds.

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexanoic acid (DHA) and 7,10,13,16,19-docosapentanoic acid (DPA).

As used herein, the term "moiety" when used in reference to a fatty acid refers to the portion of the fatty acid bound to another molecule via a bond, such as an ester or ether linkage to for example, a glyceride or phosphoglyceride molecule.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "functional food" refers to a food product to which a biologically active supplement has been added.

As used herein, the term "infant food" refers to a food product formulated for an infant such as formula.

As used herein, the term "elderly food" refers to a food product formulated for persons of advanced age.

As used herein, the term "pregnancy food" refers to a food product formulated for pregnant women.

As used herein, the term "nutritional supplement" refers to a food product formulated as a dietary or nutritional supplement to be used as part of a diet.

DETAILED DESCRIPTION OF THE INVENTION

The present invention relates to enhanced omega-3 formulations, and in particular to formulations comprising a phospholipid fraction and a triglyceride fraction in combinations with agents that provide a formulation with improved viscosity and dispersion characteristics. Accordingly, in some embodiments, the present invention provides a lipid formulation comprising about 25 to 55% w/w of a first lipid fraction comprising from about 50%, 52%, 54%, 56%, 60% or 70% to 100% w/w phospholipids derived from a marine source; about 40% to 70% w/w of a second lipid fraction comprising from about 70% to 100% triglycerides; and an additional component(s) selected from about 1% to 8% w/w of an alcohol and/or from about 1% to 20% of a surfactant. In some preferred embodiments, the lipid formulations comprises a total EPA and DHA content of from about 350 mg to 700 mg per gram of the formulation, from about 400 mg to 600 mg per gram of the formulation, or preferably from about 425 mg to 575 mg per gram of the formulation. In some embodiments, the formulations may be provided as a solid dosage form, preferably as a soft gel capsule. Exemplary soft gel capsules may contain, for example, 300, 400, 500, 600, 800, 1000, 1200 or 1500 mg of the formulation. In some preferred embodiments, the lipid formulation has a viscosity of from about 20 to 200, 300, 400, 500 or 1000 mPas at 30° C. In some particularly preferred embodiments, the lipid formulation has a viscosity of from about 50 to 150 mPas at 30° C.

In some embodiments, the first and second lipid fractions are extracted from different source materials. In some embodiments, the first and second lipid fractions are fractions that are separately extracted from the same source material. In some embodiments, first lipid fraction is extracted from a marine source selected from the group consisting of krill, squid and herring.

First Lipid Fraction

In some preferred embodiments, the first lipid fraction is a krill phospholipid fraction. In some embodiments, the krill lipid fraction preferably comprises from about 50%, 52%, 54%, 56%, 60% or 70% to 100% phospholipids w/w, the phospholipids being further characterized in having a combined EPA and DHA content of from about 25% to 40% w/w of the krill phospholipid fraction. In some embodiments, the first lipid fraction is preferably substantially free from triglycerides. For example, the first lipid fraction may preferably comprise less than about 3%, 2%, 1%, or 0.5% triglycerides on a w/w basis. In some further preferred embodiments, the krill phospholipid fraction preferably comprises a mixture of phospholipid compounds of formula (I):

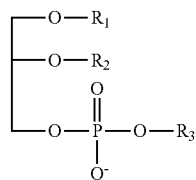

wherein:
  $R_1$ and $R_2$ are each independently selected from a fatty acid moiety of formula $-COC_nH_m$, a fatty acid moiety of formula $-CH_2C_nH_m$, and $-H$;
  $R_1$ and $R_2$ include omega-3 fatty acid moieties, such that at least 30% by weight of the phospholipid compounds is composed of omega-3 fatty acid moieties;
  at least 90% by weight of total omega-3 fatty acid moieties are at position $R_2$;
  $R_1$ and $R_2$ are not both $-H$ in a phospholipid compound, and $R_1$ or $R_2$ is $-H$ in less than 3% by weight of the compounds of formula (I);
  $R_3$ is selected from $-H$, a choline moiety, an ethanolamine moiety, a N-acetylethanolamine moiety, an inositol moiety, and a serine moiety; and
  $R_3$ is a choline moiety in at least 85% by number of the compounds of formula (I).

and wherein the composition also has one or more of the following properties:
  (a) at least 50%, 52%, 54%, 56%, 60% or 70% by weight of the krill phospholipid fraction consists of phospholipid compounds of formula (I);
  (b) the weight ratio of C16:0/C14:0 fatty acid moieties in the krill phospholipid fraction is between 10:1 and 18:1 and/or the weight ratio of C18:4 n-3/C18:3 n-3 fatty acid moieties is between 1:1 and 3:2;
  (c) the krill phospholipid fraction includes less than 300 μg astaxanthins per gram of phospholipid;
  (d) the krill phospholipid fraction comprises less than 0.01% by weight trimethylamine N-oxide;
  (e) the krill phospholipid fraction comprises less than 0.01% by weight homarine;
  (f) the krill phospholipid fraction includes less than 5% by weight water;
  (g) the krill phospholipid fraction has less than about 0.03% by weight PUFA polymers
  (h) the krill phospholipid fraction includes both phospholipids where $R_1$ is a fatty acid moiety of formula $-COC_nH_m$ and phospholipids where $R_1$ is a fatty acid moiety of formula $-CH_2C_nH_m$;
  (i) the krill phospholipid fraction includes both phospholipids where $R_1$ is an omega-3 fatty acid moiety and phospholipids where $R_2$ is an omega-3 fatty acid moiety;
  (j) the krill phospholipid fraction includes less than 5% by weight sphingomyelin;
  (k) the krill phospholipid fraction is free from chloroform and hexane; and/or
  (l) less than 8%, 5%, 3%, 2%, 1% or 0.9% by weight of phospholipids in the krill phospholipid fraction is formed of compounds where $R_1$ or $R_2$ is $-H$, or more than 1.1% by weight of phospholipids in the composition is formed of compounds where $R_1$ or $R_2$ is $-H$.

$R_1$ and $R_2$ $R_1$ and $R_2$ are each independently selected from the group consisting of a fatty acid moiety of formula $-COC_nH_m$, a fatty acid moiety of formula $-CH_2C_nH_m$, and $-H$. $R_1$ or $R_2$ is $-H$ in only a small fraction of the compounds of formula (I) i.e. less than 3% by weight of the phospholipid compounds are lysophospholipids (see below). Thus most $R_1$ and $R_2$ are $-COC_nH_m$ or $-CH_2C_nH_m$. Where $R_1$ or $R_2$ has formula $-COC_nH_m$ the fatty acid moiety has an ester linkage, but where $R_1$ or $R_2$ has formula $-CH_2C_nH_m$ the fatty acid moiety has an ether linkage. In these formulae $C_nH_m$ refers to the aliphatic chain which is seen in a naturally-occurring fatty acid (e.g. as seen in krill). For any value of n, m=2n+1 when the fatty acid moiety's aliphatic chain is saturated, but m is reduced by 2 for each unsaturated bond (double bond) in the aliphatic chain i.e. m=2n−1 if one unsaturated bond is present, m=2n−3 if two double bonds are present, m=2n−5 if three double bonds are present, etc. Thus, in general, n is an integer in the range of 4-24 and m=2(n−p)+1, where p is the number of double bonds in the fatty acid moiety. The value of n for krill is generally within the range of 11 to 21, and krill phospholipids can include fatty acid moieties with up to six double bonds.

Typically, where a fatty acid moiety at position $R_1$ or $R_2$ is of formula $-CH_2C_nH_m$, the fatty acid moiety is either saturated or monounsaturated. Thus, where $R_1$ or $R_2$ is of formula $-CH_2C_nH_m$, the relationship between n and m is m=2n+1 at that position. In a single molecule, however, it is possible to have a fatty acid moiety of formula $-COC_nH_m$ at one of $R_1$ and $R_2$ (i.e. ester-linked) and a fatty acid of formula $-CH_2C_nH_m$ at the other of $R_1$ and $R_2$ (i.e. ether-linked). Overall, within the mixture, it is preferred that no more than 10% by number of the fatty acid moieties are of formula $-CH_2C_nH_m$ (i.e. 10% or fewer of fatty acid moieties are ether-linked, and more than 90% are ester-linked).

In general, $R_1$ and $R_2$ are not both of formula $-CH_2C_nH_m$ in any single phospholipid molecule. Furthermore, fewer than 5% by number (e.g. fewer than 1% by number, or even zero) of the phospholipid molecules in the mixture have $R_2$ of formula $-CH_2C_nH_m$. In other words, ether-linked fatty acid moieties within the mixture may be seen at $R_1$, but not at $R_2$. Thus, in some embodiments: $R_1$ is selected from a fatty acid moiety of formula $-COC_nH_m$, a fatty acid moiety of formula $-CH_2C_nH_m$, and $-H$; and $R_2$ is selected from a fatty acid moiety of formula $-COC_nH_m$, and $-H$.

In some embodiments: $R_1$ is selected from a fatty acid moiety of formula $-COC_nH_m$, a fatty acid moiety of formula $-CH_2C_nH_m$ where m=2n+1, and $-H$; and $R_2$ is selected from a fatty acid moiety of formula $-COC_nH_m$, and $-H$. Thus, within the mixture: $R_1$ is an ester-linked fatty acid, an ether-linked saturated or monounsaturated fatty acid, or hydrogen; and $R_2$ is either an ester-linked fatty acid moiety or hydrogen; provided that $R_1$ and $R_2$ are not both hydrogen in a single molecule.

The term "fatty acid" refers to a carboxylic acid with an unbranched aliphatic chain, which may be saturated or unsaturated. These have the general formula $C_nH_m-COOH$ Long chain polyunsaturated fatty acids (LC-PUFAs) are in general fatty acids that have a n value of 19 or more. Polyunsaturated refers to unsaturation at two or more bonds. The term "fatty alcohol" refers to an alcohol with an unbranched aliphatic chain, which may be saturated or unsaturated, and they have the general formula $C_nH_m-CH_2OH$. The term "fatty acid moiety" as used herein refers to the aliphatic chain $C_nH_m$ from such fatty acids and fatty alcohols, and the nature of the moiety can be defined by referring to the corresponding fatty acid and/or fatty alcohol. Thus, for a fatty acid moiety of formula $-COC_nH_m$ or $-CH_2C_nH_m$ the corresponding fatty acid is $C_nH_m-COOH$ and the corresponding fatty alcohol has formula $C_nH_m-CH_2OH$. By way of example the fatty acid DHA ($C_{21}H_{31}COOH$) corresponds to a fatty acid moiety of formula $-COC_{21}H_{31}$ or $-CH_2C_{21}H_{31}$, and EPA ($C_{19}H_{29}COOH$) corresponds to a fatty acid moiety of formula $-COC_{19}H_{29}$ or $-CH_2C_{19}H_{29}$.

$R_1$ and $R_2$ can thus be fatty acid moieties that contain saturated or unsaturated aliphatic chains, but at least 30% by weight of the phospholipid mixture is composed of omega-3 fatty acid moieties at the $R_1$ and $R_2$ positions (i.e. omega-3 fatty acid moieties provide at least 30 g for every 100 g of phospholipid compounds in the mixture). Omega-3 fatty acids are polyunsaturated fatty acids whose final double bond is positioned between the third and fourth carbon atoms from the methyl end of the hydrocarbon chain. Non-limiting examples of omega-3 fatty acids include 5,8,11,14,17-eicosapentaenoic acid (EPA), 4,7,10,13,16,19-docosahexanoic acid (DHA) and 7,10,13,16,19-docosapentanoic acid (DPA). At least 90% by weight of total omega-3 fatty acid moieties in a phospholipid mixture are at position $R_2$ within formula (I). At least 50% by weight of total omega-3 fatty acid moieties in a phospholipid mixture are EPA and/or DHA (i.e. weight of DHA and EPA/total weight of omega-3 fatty acid moieties in the phospholipids of formula I).

The weight contribution of total omega-3 fatty acid moieties at the $R_1$ and $R_2$ positions can be determined by extracting total phospholipids from the krill lipid fraction. See, e.g., Bligh & Dyer (1959) Can. J. Biochem. Physiol. 37:911-917. This is followed by hydrolysis of the lipids to release fatty acids. The released fatty acids are converted to fatty acid esters e.g. fatty acid methyl esters and these esters are analysed e.g. by gas chromatography, HPLC, etc. For instance, the American Oil Chemists' Society has published AOCS Official Method Ce 1b-89 for determining the fatty acid composition of marine oils and marine oil esters by capillary column gas-liquid chromatography. Similarly, quantitative analysis of krill oil may be performed using other HPLC methods. See, e.g., Winther et al. (2011) Lipids 46:25-36; Homan R et al 1998 J Chromatogr B Biomed Sci Appl 708:21-26; and Moreau et al 2006 Lipids 41:727-734. These established methods provide the amount of specific fatty acids present in a sample, from which the amount of omega-3 fatty acids present in the sample (i.e. in positions $R_1$ and $R_2$ of the phospholipid mixture) can be calculated. In general, references to the content of lipid or phospholipid compositions on a weight/weight basis as referred to herein should be taken as having been determined on the basis of these methods (extraction followed by processing and analysis by chromatography).

In some embodiments, the krill phospholipid fraction may be produced as described in PCT/IB2014/002130, incorporated herein by reference in its entirety. In further preferred embodiments, the krill phospholipid fraction is produced as follows.

The process for preparing a composition which is rich in polar lipids from a biological material containing those lipids, e.g., a krill phospholipid fraction, preferably comprise the steps of:

(a) mixing the biological material (e.g., a krill material) with a first solvent system in which the polar lipids are soluble, thereby preferentially extracting the polar lipids into a liquid phase of a slurry;

(b) washing the biological material with a second solvent system in which the polar lipids are poorly soluble; and (c) mixing the extracted and washed material from steps (a) and (b) with a third solvent system which partitions neutral lipids and polar lipids, wherein steps (a) and (b) can be performed in either order before step (c).

The process takes advantage of the different solubility of the various components of the biological material in three different solvent systems. For example, the polar nature of the desired lipids means they can behave differently from neutral lipids in certain solvents. These differences allow the different lipids to be separated effectively during the process of the invention, resulting in material having a high content of the desired lipids, and in which the content of undesirable components is reduced. In particular the relatively high solubility of the desired polar lipids in certain solvents (the first solvent system e.g. concentrated organic protic solvents) allows their efficient extraction from biological materials, whereas their relatively low solubility in other solvents (the second solvent system e.g. a dilute organic protic solvent) means that such solvents can be used to wash out various undesired components from the lipid material. Finally, although the polar lipids and various neutral lipids may both be soluble in the first solvent system, they have different properties which means that they can be separated in a further treatment step, which also serves to reduce the concentration of other undesired components. Overall, the process of the invention can efficiently reduce the amount of (or even remove) various undesired components including trimethylamine N-oxide (TMAO), astaxanthins, lysophospholipids, free fatty acids, cholesterol and cholesterol esters, and neutral lipids. Furthermore, the process can be used with three solvent systems which are all readily acceptable for pharmaceutical purposes and whose solvent components (particularly their organic components) can if necessary be removed to safe residual levels.

The process has been designed to increase the proportion of phospholipids in the final composition relative to undesired components. At any stage of the process, the ratio of phospholipids to any specific undesired component can be determined and the ratio calculated. The ratio is in general calculated on a weight/weight basis. Where possible, undesired components can be removed completely i.e. to be un-quantifiable in the final composition (using currently available analytical techniques i.e. below the limit of quantification or LOQ).

Step (a)

Step (a) of the process involves mixing a biological material (e.g., a krill material) with a first solvent system in which the polar lipids are soluble, to preferentially extract polar lipids into a liquid phase of a slurry. The desired polar lipids in the biological material are thus solubilised for further processing and extraction. The solubility of the biological material's various components in the first solvent system will determine their location at the end of step (a). Components that are soluble in the first solvent system (including the desired polar lipids) will tend to be extracted from the biological material, so that they are present in the liquid phase at the end of step (a). Other components will preferentially remain in the slurry residue. Key components which are present primarily in the slurry after step (a) are triglycerides, proteins/peptides, and insoluble materials such as shell fragments (calcium carbonate, chitosan, etc.), but also cholesterol esters.

The desired lipids are soluble in the first solvent system and so they are preferentially extracted into the slurry's liquid phase, from which they can be processed further. The term "preferentially" is used to reflect the fact that the desired polar lipids tend to be more soluble than neutral lipids in the liquid phase. The polar lipids will thus tend to enter the liquid phase, rather than remaining with the biological material slurry. Other lipids present in the biological material (e.g. neutral lipids) tend to be less soluble in the liquid phase and so some of these remain with the slurry. The term "preferentially" thus also reflects the fact that although some neutral lipids might be present in the liquid phase at the end of step (a), the liquid phase will contain a higher ratio of polar lipids:neutral lipids compared to the ratio in the biological material at the start of step (a). In contrast, the slurry residue will contain a lower ratio of polar lipids: neutral lipids compared to the starting biological material. For example, krill material may contain a weight ratio of phospholipids:neutral lipids which is approximately 1:1 before step (a), whereas this can be 4:1 or higher in the liquid phase after step (a). The ratio of phospholipids to neutral lipids in the liquid phase after step (a) is thus higher than in the material before step (a). Moreover, the ratio of phospholipids to triglycerides can be about 10:1 in the liquid phase after step (a).

The solvent system used in step (a) (the 'first' solvent system) is any solvent system whose addition to the biological material results in a liquid phase in which polar lipids are preferentially soluble relative to neutral lipids. The solvent system can be a mixture of solvent components. The first solvent system will generally comprise at least one protic solvent component and an organic solvent component (or, more usually, an organic protic solvent).

Typical organic protic solvents or solvent components for use in step (a) include, but are not limited to, n-butanol, n-propanol, isopropanol, nitromethane, ethanol, and methanol.

Hydroxy-containing protic solvents are preferable, and the most preferred organic solvent for use with the invention is ethanol. The amount and concentration of organic protic solvent components which are used is enough to provide a first solvent system which can preferentially extract the desired lipids into a liquid phase of a slurry. The amount and concentration of organic solvent components will take into account the amount of moisture that is present in the biological material at the start of step (a).

In one embodiment, the first solvent system comprises ethanol and water, ideally with a final ethanol concentration of between 70-95% w/w, or 80-90% w/w (based on total weight of solvent). If the starting material already includes water (which will usually be the case), the amount of ethanol that is added will take this water into account, and will also take into account the amount of any water in the ethanol (see below). By way of example, the weight ratio of ethanol: biological material is generally within the range of 1:1 to 10:1, preferably within the range of 2:1 to 8:1, or between about 3:1 to about 4:1. For instance, between 3-4 kg of absolute ethanol can be added per kg of wet krill material having a water content of 65% in order to provide the first solvent system, taking into account the water content of the krill material.

Step (a) may conveniently be performed at temperatures of up to 50° C. The biological material and solvent components which are added may be at different temperatures when they are first combined. For instance, the biological material might be frozen i.e. at a temperature of less than 0° C. e.g. less than about −5° C., −10° C., −15° C., −20° C., or −25° C. Solvent components should be liquid when they are added to the biological material, and are preferably at a temperature of between 0-50° C. e.g. at between 10-45° C., between 15-35° C. or 20-25° C. After mixing, however, the mixture can be incubated under room temperature conditions or within any temperature range referred to above e.g. at between 10-45° C. The temperature chosen for step (a) can represent a balance between higher yields and lower purity, and incubation at between 20-25° C. gives good results using krill material and ethanol.

Mixing of the biological material and the first solvent system ensures that they become distributed within each other. In some circumstances this might be achieved simply by combining two components, but usually it requires active mixing e.g. by stirring, inversion, or other appropriate means. Mixing is preferably achieved using stirring, which is preferably carried out at 50 to 500 rpm, or 100 to 200 rpm. Stirring or other active mixing steps may be continued for as long as desired to ensure adequate contact between different components, and this can usually be achieved in an hour or less, although longer periods can also be used (e.g. up to several weeks). Stirring in step (a) for 45 minutes can achieve a good extraction of polar lipids, but longer periods can increase the amount of material which is extracted e.g. for between 2-6 hours, such as for 3-4 hours.

After the biological material and the organic solvent components have been mixed, a slurry forms in which the desired lipids are preferentially present in a liquid phase. The liquid phase also contains other components from the biological material that are soluble in the first solvent system e.g. other polar lipids, some neutral lipids, some proteins, water soluble amines, and ionic species. This liquid phase is separated from the slurry and is processed further in downstream steps. Separation of the liquid phase from the slurry can be achieved by any suitable means for separating solids and liquids e.g. centrifugation, filtration, decanting, draining, etc.

If desired the slurry residue can be recycled, such that it is re-used as biological material for one or more repeats of step (a). In this manner it is possible to extract polar lipids which remain within the slurry residue. Such further extracted material can then continue into subsequent steps e.g. after being combined with other material arising from previous extractions.

If step (a) comes before step (b), the starting biological material is extracted as defined above, and the extracted polar lipids are then washed as described below in step (b). On the other hand, if step (a) comes after step (b), the starting biological material will previously have been washed as described below for step (b), it will then be extracted as discussed above, and these washed and extracted polar lipids will then be taken into step (c) as described below.

Step (b)

Step (b) of the process involves washing the biological material with a second solvent system in which the polar lipids are poorly soluble. This biological material may be the product of step (a), or may be biological material which is to be washed before extraction step (a) takes place.

The key difference between step (a) and (b) is that the desired polar lipids are highly soluble in the first solvent system but are poorly soluble in the second solvent system, while undesired components (such as salts, metal ions, carbohydrates) will dissolve in the second solvent system. Thus step (b) permits the biological material to be washed (before or after step (a) solubilises them), and this washing is useful for e.g. de-salting the material.

The choice of second solvent system can depend on whether step (b) occurs before or after step (a). For instance, if step (b) occurs before step (a) then the second solvent system might be achieved using water, or a weak aqueous solution of organic solvent, to wash the biological material, thereby dissolving undesired components into the water. The aim of this early washing is to remove undesired components which are soluble in water, without solubilising a significant amount of the desired polar lipids. If step (b) occurs after step (a), however, it is easier if the second solvent system is derived from the first solvent system e.g. by using a strong ethanol solution as the first solvent system and a weak ethanol solution as the second solvent system.

The change between the first and second solvent systems can be achieved in various ways. For example, if step (a) precedes step (b) then the first solvent system can be removed (e.g. by evaporation) and then the second solvent system can be added, but in some embodiments it is possible to simply dilute the first solvent system until the second solvent system is formed e.g. by adding more water to a strong ethanol solution (the first solvent system) to form a weak ethanol solution (the second solvent system). If step (a) follows step (b) then the second solvent system can be removed (e.g. by evaporation) and then the first solvent system can be added, but in some embodiments it is possible to simply add extra solvent components until the first solvent system is formed e.g. by adding more concentrated ethanol to a weak ethanol solution or to water (possible second solvent systems) to form a strong ethanol solution (the first solvent system).

Where solvent removal is used between steps (a) and (b) then evaporation is a convenient technique when the solvent includes components which are more volatile than water. Evaporation can provide material which is solid at room temperature and is moderately rich in polar lipids, suitable for washing. For instance, up to about 85% by weight of this lipid-rich material can be phospholipids of interest. The second solvent system can then be added to this material.

In general, however, the preferred way of making the second solvent system when step (b) follows step (a) is by dilution of the first solvent system. Dilution of the first solvent system, to reduce the overall concentration of its solvent components, is achieved by adding a diluent. Examples of suitable diluents include aqueous diluents such as water, but solutions of a solvent component (e.g. an organic protic solvent) which may be the same as or different to the solvent component used in step (a) may also be used. Preferably the concentration of a solvent component (e.g. an organic protic solvent such as ethanol) in the mixture after dilution is between 50-70% w/w (solvent/total weight of the liquid material). Appropriate solvent mixtures and concentrations for washing the phospholipids to remove impurities, without too much loss of the desired lipids, can vary with temperature and with the chosen solvent system, but can readily be assessed.

Thus the second solvent system when step (b) follows step (a) may be an aqueous solution of ethanol, where the concentration of ethanol is between 50-70% w/w, preferably between 55-65%, between 58-62%, or about 60%. Under typical conditions, ethanol concentrations above about 70% tend to lead to the loss of too much polar lipids in the waste, whereas concentrations below about 60% can lead to the formation of emulsions from which the polar lipids are difficult to extract.

The second solvent system when step (b) precedes step (a) may be a weak aqueous solution of ethanol (e.g. up to 10% w/w EtOH), but ideally use water.

Mixing with the second solvent system generally involves stirring to ensure that the materials become distributed within each other. Stirring is preferably carried out at 50 to 500 rpm, or 100 to 200 rpm. Stirring may be continued for as long as desired to ensure adequate contact, and this can usually be achieved less than an hour, although longer periods can also be used (e.g. several weeks). After stirring the mixture is allowed to settle, and it separates into phases which include a lipid-rich phase that can be processed further. The other phase(s) are referred to herein as the waste, which includes material which has been washed away using the second solvent system.

Compared to the material prior to step (b), the lipid-rich phase has an increased proportion of desired polar lipid components relative to certain undesired components. The solubility of certain undesired components in the second solvent system is such that they will tend to enter the waste phase(s), whereas the polar lipid components will tend to remain in the desired lipid-rich phase. The waste thus contains certain undesired components that are more water-soluble than the desired polar lipids. Examples of such components include salts such as TMAO, water soluble proteins and peptides, water soluble amines, salts such as NaCl and $CaCl_2$, other ionic species, and also lysophospholipids. The lipid-rich phase (which can be approximately 60% lipids and 40% solvent when step (b) follows step (a)) contains the desired phospholipids but also contains some neutral lipids (e.g. at a ratio of approximately 4:1 phospholipids to neutral lipids when step (b) follows step (a)).

The lipid-rich phase and the waste are separated before proceeding. This can be achieved simply by letting the mixture settle or by centrifugation, to produce a lipid-rich phase and a waste phase which are then separated e.g. by decanting, draining the lipid-rich phase, or suction of the waste phase. In general if the mixture is allowed to settle then the lipid-rich phase is underneath the waste phase. The mixture is generally allowed to settle for a sufficient period of time to allow the effective separation of the two phases. This may be at least 4 hours (e.g. at least 6, 8, 10, 12, 14, 16, 18, 20, 22, 24, 30, 36, 48, 54, 60 hours). This may be carried out at any suitable temperature, e.g. less than 50° C., 40° C., 30° C., 20° C., 10° C., 5° C. If step (b) precedes step (a) the liquid water phase is the waste, containing dissolved impurities. This is removed from the slurry, which is processed further in downstream steps. Separation of the liquid phase from the slurry can be achieved by any suitable means for separating solids and liquids e.g. centrifugation, filtration, decanting, draining, etc.

The lipid-rich phase contains a high proportion of desired polar lipids. This phase can be re-washed using step (b) again. The solvent system used for re-washing can conveniently be the same as the solvent system which was used for previous washing. For instance, if step (b) first used a 60% w/w ethanol solution then re-washing can also be achieved by adding ethanol and/or water to the lipid-rich phase to achieve a final concentration of 60% w/w ethanol. This can again provide a lipid-rich phase and a waste phase.

Thus, if desired, washing step (b) can be performed more than once, such that a washed lipid-rich phase is re-washed at least once under the same or similar conditions. Thus step (b) may include more than one wash e.g. it can include between 2-10 (e.g. 3-9, 4-8, 5-7) washings with a second solvent system. Performing multiple washes can remove undesired components which would otherwise remain in the lipid-rich phase. Repeated washings can also have a minor impact on the ratio of polar lipids to neutral lipids, as a small amount of polar lipids may enter the waste phase, but in general step (b) does not have a large impact on this ratio (e.g. when step (b) follows step (a) a change from 82:18 to 78:22 has been seen, so only a small amount of phospholipid was lost). Where multiple washings are used, it is possible to reduce the washing time as further steps are added e.g. an 8 hour duration for the first wash, then 7 hours for the second, and 6 hours for subsequent washes, etc.

Washing step (b) may be carried out at any suitable temperature but is optionally carried out at temperatures within the range of 5-25° C.

As noted above, an example of an undesired component affected by step (b) is TMAO (trimethylamine N-oxide, $(CH_3)_3NO$). This is an osmolyte found in saltwater fish, sharks and rays, molluscs, and crustaceans, which is believed to have a role in counteracting the protein-destabilizing effects of pressure. TMAO is highly soluble in water and will thus tend to enter the waste rather than the lipid-rich phase during step (b). The ratio of phospholipid:TMAO on a w/w basis is thus lower in the starting material than in the washed liquid phase which is produced in step (b). Based on experience with krill material, 85% of TMAO can be removed with a single washing step, and repeated washing can remove TMAO to levels below the LOQ.

Step (b) can also efficiently remove salts, such as sodium chloride, which can be seen by measuring conductivity of the material e.g. step (b) can reduce the material's conductivity to the same level as de-ionised water. Wet krill material can have a NaCl concentration of 1.5% by weight or more, but step (b) can reduce conductivity from several hundred µS/cm down to about 10 µS/cm.

Step (c)

The combination of steps (a) and (b) provides an extracted and washed material which is rich in desired polar lipids, but which can still contain undesired components such as monoglycerides, diglycerides, triglycerides, free fatty acids, and astaxanthins. Step (c) thus uses a third solvent system to separate these undesired components from the desired polar lipids by mixing the extracted and washed material from steps (a) and (b) with a third solvent system which partitions the neutral lipids and the polar lipids. Step (c) thus increases the proportion of desired polar lipids relative to the undesired components.

The third solvent system partitions polar lipids and neutral lipids into two or more separable phases. For example the polar lipids and neutral lipids may each be present in a liquid phase, wherein the two phases are separable (e.g. two separate phases in a multi-phase liquid system). As an alternative, the third solvent system may cause a precipitate to form, which may be enriched either for polar lipids or neutral lipids. The two phases (e.g. two liquids, or a solid precipitate and a liquid) are then separated to recover the desired polar lipid component.

Preferably the third solvent system comprises a ketone (e.g. of formula $R^4—(CO)—R^5$ where $R^4$ and $R^5$ are any groups other than H, but are preferably independently selected from a $C_1$-$C_6$ alkyl or alkenyl group, an aryl group, or together form a cycloalkyl) or a low molecular weight ester (e.g. $R^6—(CO)—O—R^7$ where $R^6$ and $R^7$ are independently selected from a $C_1$-$C_6$ alkyl group). A preferred example of a ketone is acetone. A preferred example of a low molecular weight ester is ethyl acetate. A further but less preferred example of a suitable solvent system is methanol.

Step (c) is carried out by mixing the material arising from steps (a) and (b) with the third solvent system. For instance, acetone or ethyl acetate can be added to the washed lipid-rich phase. In general, the lipid-rich phase is mixed with at least one volume of solvent, and ideally with a volume excess of solvent e.g. using a volume of solvent which is 2-fold to 8-fold the volume of the lipid-rich phase, such as from 2-fold to 5-fold. This mixing can be achieved simply by combining the components, but it is preferable to use active mixing e.g. by stirring, inversion, or other appropriate means. Mixing is typically achieved by stirring, which is preferably carried out at 50 to 500 rpm, or 100 to 200 rpm. Stirring or other active mixing steps may be continued for as long as desired to ensure adequate contact between different components, and this can usually be achieved in an hour or less, although longer periods can also be used.

Preferably step (c) results in precipitation of the desired polar lipids, although it is possible instead that the polar lipids remain in solution and the undesired components are removed as precipitates. For example when acetone or ethyl acetate is used, the polar lipids precipitate and undesired components are present at reduced concentration in the precipitate. On the other hand if methanol is used as the third solvent system then desired polar lipids remain in solution and undesired lipids are precipitated.

A preferred step (c) uses acetone as the third solvent system to precipitate desired polar lipids, and the precipitated material is collected for further use.

Temperature control can be important during step (c). Typically, substantially all of the washed lipid-rich material is dissolved in the third solvent system, for which temperatures of room temperature or above will usually suffice. The temperature is then reduced in order to permit phases to separate. For example, the material can be dissolved in acetone at room temperature, and then the solution can be cooled to cause the desired polar lipids to precipitate. The upper liquid phase (i.e. the acetone with its dissolved undesired components) can then be discarded (e.g. removed by suction), leaving precipitated polar lipids in purer form. Thus the third solvent system is ideally used at two temperatures, where the colder temperature causes precipitation which increases the proportion of desired polar lipids relative to the undesired components. Cooling to below 10° C. e.g. below 5° C., or even below 0° C. is typical.

Addition of the third solvent system can be performed more than once within step (c). Thus a polar lipid-rich composition can be separated from the other components of the mixture, and then mixed again with at least one volume of solvent. For example, where the desired lipid-rich phase is a precipitate, excess solvent can be removed and then the precipitate can be re-dissolved in at least one volume of further solvent, and then re-precipitation can be performed. Dissolution may be achieved by adding further third solvent system to the precipitate, followed by heating to a temperature at which the precipitate re-dissolves (e.g. about 10-25° C., 15-22° C., 18-20° C.). The solution is then re-subjected to conditions at which the polar lipid rich phase precipitates. Overall, precipitation may be carried out from 2-6 (e.g. 3-5 or 4-5) times in order to sequentially increase the purity of desired polar lipids.

The third solvent system displays differential solubilisation of the desired polar lipids compared to neutral lipids. In cold acetone, for instance, phospholipids are generally insoluble whereas various undesired components are soluble e.g. neutral lipids, astaxanthins, and free fatty acids (particularly free unsaturated fatty acids; some free saturated fatty acids may precipitate with phospholipids).

The material that is obtained by this step (e.g. the precipitate after cold acetone precipitation) generally contains at least 90% phospholipid w/w (weight of phospholipids/total weight of lipids in the precipitate) e.g. ≥95%, ≥96%, ≥97%, ≥98%, or even ≥99%. Moreover, and in contrast to the material produced in WO2011/050474, it generally includes low levels of astaxanthins. Furthermore, free fatty acids are typically undetectable (i.e. below the LOQ).

Step (c) provides a composition which is rich in desired polar lipids, but this material will contain residual solvent(s) from the third solvent system (e.g. acetone) and usually includes some residual water. Thus the process ideally includes a further step (d) comprising removal of residual organic solvent component(s) and/or water from the composition.

To remove residual organic solvent components and/or water, two techniques will in general be required: a first which removes organic solvent and one which then removes water but can also remove final residual organic solvent. For example, removal of organic solvent can conveniently be achieved by techniques such as evaporation (e.g. on a rotary evaporator, rather than falling film evaporation due to the solid nature of the material). Water removal can then be achieved by lyophilisation, which can also remove any residual organic solvent (such as acetone). Thus evaporation and freeze drying can be carried out sequentially.

Compared to the material produced after step (c), performing step (d) can provide a lipid-rich composition which has an acetone content of less than about 0.1% by weight e.g. less than 0.01%, or less than 0.005% (see below) and/or less than about 5%, 4%, 3%, 2%, 1%, 0.5% by weight water. This material is suitable for pharmaceutical use.

General Conditions for the Process

As set out above, steps (a) and (b) are performed in either order. Thus the process may comprise steps (a)-(b)-(c) or steps (b)-(a)-(c). Preferably the process comprises steps (a)-(b)-(c) in that order.

Unless specified otherwise herein steps (a) to (c) of the process are generally performed at room temperature (e.g. at between 10-25° C., such as between 15-22° C., or about 18-20° C.), but as noted above that step (c) will usually be performed at lower temperatures as noted above and step (b) may also be performed at lower temperatures. Although the temperature during any step may be controlled, it is not essential that it remains constant during the step. Nevertheless, the temperature during any step is preferably controlled such that the temperature does not deviate more than ±2.5° C. for at least half of the total duration of that step. Ideally, the temperature from starting step (a) to completing step (c) (and completing step (d), if it is performed) does not rise above 50° C.

The process is in general carried out at or around atmospheric pressure.

Because the invention aims at polar lipids of pharmaceutical grade, solvents and other materials used during a process of the invention should be of an appropriate quality e.g. pharmacopoeial quality or better. Furthermore, it is preferred to use only pharmaceutically acceptable solvent components which are regarded as safe in humans, so that residual solvent is not a safety risk. ICH topic Q3C defines guidelines for residual solvents, and groups solvents into three classes. Pharmaceutically acceptable organic solvent components used in processes of the invention are thus preferably selected only from Q3C 'class 3' (i.e. acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methylisobutyl ketone, cumene, 2-methyl-1-propanol, dimethyl sulfoxide, pentane, ethanol, 1-pentanol, ethyl acetate, 1-propanol, ethyl ether, 2-propanol, ethyl formate, propyl acetate, and formic acid). Thus solvent components such as chloroform and hexane can be avoided. Ideally, the processes use as few organic solvent components as possible e.g. only 2 or 3 organic solvent components in total. Thus a process in which ethanol and acetone are the only 2 organic solvent components is advantageous for preparing a final pharmaceutical product.

Where ethanol is used as a solvent component (e.g. in the first or second solvent system), it is possible to use aqueous ethanol, or absolute ethanol (i.e. ethanol having a water content of <1% by weight). For instance, step (a) can be performed using 99.5%, 99.8% or even 100% ethanol. For cost reasons, however, it is preferred to use aqueous ethanol e.g. 95% ethanol (which usually contains 92.0-92.7% w/w or 94.7-95.2% v/v ethanol). Concentrations will be calculated accordingly, taking water into account. Pharmacopoeial-grade ethanol is widely available.

Where steps (a) to (c) involve separating two components, active mixing should typically cease to allow those components to separate e.g. to allow two liquid phases to separate, or to allow a precipitate to settle.

Preferably at least one of steps (a) to (d) is performed under an atmosphere containing less oxygen than air. Thus a step may be performed under an inert gas e.g. under nitrogen. These conditions can help to reduce peroxidation of PUFAs to form lipid peroxides, which then can polymerise to produce polymerised PUFAs. Preferably, all of steps (a) to (d) are performed under an inert gas.

Similarly, it is preferred to use degassed solvent components (e.g. degassed ethanol). In particular, the amount of dissolved oxygen in the solvent should be less than 150 µl/ml e.g. <50 µl/ml. This can be achieved by various methods e.g. by purging the solvent by bubbling nitrogen or argon through it for at least half an hour, or by atmosphere exchange under sonication.

It is preferred that the process should not be performed under bright light, although darkness is not required. Again, this helps to avoid polymerisation of PUFAs.

Second Lipid Fraction

In some embodiments, the second lipid fraction is preferably a triglyceride omega-3 concentrate. Suitable methods for making triglyceride omega-3 concentrates are known in the art and generally involve up concentration of omega-3 ethyl esters following by re-esterification to glycerol. See, e.g., WO/2009/139641 and WO/2008/060163, the entire contents of which are incorporated herein by reference. The present invention is not limited to concentrates made from any particular source material or omega-3 fatty acids. Suitable source materials include, but are not limited to, fish, plants, algae, squid, krill and the like. In some preferred embodiments, the triglyceride omega-3 concentrate is a fish oil concentrate. In some embodiments, the triglyceride concentrate is characterized in comprising a combined content of EPA and DHA of from about 45% to 80% w/w of the triglyceride omega-3 concentrate. In some embodiments, the triglyceride concentrate is characterized in comprising a combined content of EPA and DHA of from about 60% to 80% w/w of the triglyceride omega-3 concentrate. In some embodiments, the second lipid fraction is preferably substantially free from phospholipids. For example, the second lipid fraction may preferably comprise less than about 3%, 2%, 1%, or 0.5% phospholipids on a w/w basis.

Additional Components

During the development of the present invention, it was found that when phospholipid and triglyceride fractions were blended together, the resulting formulations suffered from several problems including high viscosity, phase separation and poor dispersion characteristics. Surprisingly, it was found that inclusion of a small amount of an alcohol in the formulation drastically lowered the viscosity of the formulations. Furthermore, inclusion of a surfactant in the formulations prevented phase separation and improved dispersion characteristics as evaluated in simulated gastric fluid.

Accordingly, in some embodiments, the formulations include an alcohol, preferably a food grade alcohol in addition to the first and second lipid fractions. Suitable alcohols include, but are not limited to, ethanol, methanol, isopropanol, etc. In some embodiments, the formulations comprise from about 1% to 8% w/w of the alcohol. In some embodiments, the formulations comprise from about 0.5% to 4% w/w of the alcohol. In some embodiments, the formulations comprise from about 1% to 3% w/w of the alcohol.

In further embodiments, the formulations include a surfactant in addition to the first and second lipid fractions. In some preferred embodiments, the surfactant is a non-ionic surfactant. Suitable non-ionic surfactants include, but are not limited to, non-inonic surfactants with a high HLB (hydrophilic-lipophilic balance) index, and non-ionic surfactants with a low HLB index. In some preferred embodiments, the surfactant is a high HLB non-ionic surfactant. i.e., a surfactant with an HLB index of ≥8. Exemplary high-HLB non-ionic surfactants include polysorbates. In some particularly preferred embodiments, the polysorbate is selected from the group consisting of polysorbate is selected from the group consisting of Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), and Polysorbate 80 (Polyoxyethylene (20) sorbitan monooleate). In other preferred embodiments, the high HLB surfactant may be Sorbitan monolaurate (Span® 20). In some preferred embodiments, the surfactant is a low HLB non-ionic surfactant, i.e., a surfactant with an HLB index of ≤8. Exemplary low HLB non-ionic surfactants include sorbitan esters such as Sorbitan monopalmitate (Span® 40), Sorbitan monostearate (Span® 60), Sorbitan monooleate (Span® 80), Sorbitan sesquioleate (Span® 83), Sorbitan trioleate (Span® 85) and Sorbitan isostearate (Span® 120). In some embodiments, the surfactant is not a free fatty acid. However, in other embodiments, the present invention contemplates use of free fatty acids as surfactants and thus the term "surfactant" as used herein includes free fatty acids, preferably from a source other than krill. In some embodiments, the free fatty acid surfactants are preferably enriched for EPA and/or DHA. In some embodiments, the formulations comprise from about 1% to 10%, 20%, 30% 40%, 50% or 60% surfactant, more preferably from about 1% to 20% surfactant and most preferably about 5% to 15% surfactant.

In some embodiments, the formulation comprises both an alcohol and a surfactant in addition to the first and second lipid fractions. Accordingly, in some embodiments, the formulations comprise from about 1% to 8% w/w, 0.5% to 4%, or 1% to 3% w/w of an alcohol as described above in combination with from about 1% to 10%, 20%, 30% 40%, 50% or 60% surfactant, more preferably from about 1% to 20% surfactant and most preferably about 5% to 15% surfactant.

The lipid formulations of the present invention are preferably made by a process wherein a predetermined amount of the first lipid fraction combined with a predetermined amount of the second lipid formulation and then mixed so that the first lipid fraction dissolves into the second lipid fraction. In embodiments where a surfactant is included, the surfactant may be blended with the second lipid fraction prior to combination with the first lipid fraction or added after the first and second lipid fractions are combined so that the blended lipid formulation comprises from about 1% to 20% of the surfactant after evaporation of the alcohol. In some embodiments, the first lipid fraction is dissolved in an alcohol, preferably a food grade alcohol, prior top combination with the second lipid fraction. After combination and mixing, the alcohol is then evaporated to provide a final blended lipid composition comprising about 25 to 55% w/w of the first lipid fraction, about 40% to 70% w/w of the second lipid fraction and from about 1% to 8% w/w of the alcohol.

In some embodiments, the formulations described above are administered to a subject in need thereof to treat a disease or condition associated with red blood cells and cell membranes, and in particular a disease or conditions associated with an abnormality in red blood cells of cell membranes. In some embodiments, the condition or disease is sickle cell disease, sickle cell anemia, or sickle cell trait. In some embodiments, the condition or disease is thalassemia (alpha-, beta- or delta-), thalassemia in combination with a hemoglobinopathy (Hemoglobin E, Hemoglobin S, or Hemoglobin C), splenomegaly, or membrane abnormalities such as acanthocytes or spur/spike cells, codocytes (target cells), echinocytes (burr cells), elliptocytes and ovalocytes, spherocytes, stomatocytes (mouth cells) and degmacytes ("bite cells").

In some embodiments, an effective amount of the formulations described above are administered to a subject in need thereof to treat or prevent a cardiometabolic disorder/metabolic syndrome. In some embodiments, the cardiometabolic disorder is selected from atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, acute coronary syndrome (ACS), non-alcoholic fatty liver disease/ non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel and diabetic autonomic neuropathy.

In some embodiments, an effective amount of the formulations described above are administered to a subject in need thereof to treat, prevent, or improve cognition and/or a cognitive disease, disorder or impairment (memory, concentration, learning (deficit)), or to treat or prevent neurodegenerative disorders. In some embodiments, the cognitive disease, disorder or impairment is selected from Attention Deficit Disorder (ADD), Attention Deficit Hyperactivity Disorder (ADHD), autism/autism spectrum disorder (ASD), (dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson disease, Lou Gehrig's disease, pre-dementia syndrome, Lewy body dementia dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well-being, neurodevelopmental, neurodegenerative disorders, hormonal disorders, neurological imbalance or any combinations thereof. In a specific embodiment, the cognitive disorder is memory impairment.

In some embodiments, an effective amount of the formulations described above are administered to a subject in need thereof to inhibit, prevent, or treat inflammation or an inflammatory disease. In some embodiments, the inflammation or inflammatory disease is selected from organ transplant rejection; reoxygenation injury resulting from organ transplantation (see Grupp et al., J. Mol. Cell. Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, Epilepsy, amyotrophic lateral sclerosis and viral or autoimmune encephalitis, preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also inflammation that results from surgery and trauma can be treated with the concentrated therapeutic phospholipid compositions.

In some embodiments, the effective amount comprises from about 0.1 to about 5 grams of the formulation, preferably from about 0.2 to about 3 grams of the formulation, and most preferably about 0.5 to about 1.5 grams of the formulation.

The formulations of the present invention may be used to treat a variety of subjects. Suitable subjects include humans as well as domestic animals, non-human primates, and companion animals such as dogs, cats and birds.

The formulations of the present invention are preferably administered orally. Accordingly, in some embodiments, the formulations of this invention (such as those described in the preceding sections) are contained in acceptable excipients and/or carriers for oral consumption. The actual form of the carrier, and thus, the composition itself, is not critical. The carrier may be a liquid, gel, gelcap, capsule, powder, solid tablet (coated or non-coated), tea, or the like. The composition is preferably in the form of a tablet or capsule and most preferably in the form of a soft gel capsule. Suitable excipient and/or carriers include vegetable oil, maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.). For intravenous or oral administration, the omega-3 compounds and compositions of the present invention may preferably be provided as emulsions.

In some embodiments, the formulations are formulated for oral administration with flavoring agents or sweeteners. The flavoring agents or sweetners may be included in the lipid formulation, the capsule material, or both. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

The compositions of the present invention may also be delivered as dietary supplements, nutritional supplements, or functional foods.

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: asorbates (ascorbic acid, mineral ascorbate salts, rose hips, acerola, and the like), dehydroepiandosterone (DHEA), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising of the compositions of the present invention. In preferred embodiments, the nutritional supplements comprise an effective amount of the components as described above. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

In still further embodiments, the present invention provides food products, prepared food products, or foodstuffs (i.e., functional foods) comprising of the fatty acids or derivatives thereof. In preferred embodiments, the foods comprise an effective amount of the components as described above. For example, in some embodiments, beverages and solid or semi-solid foods comprising the fatty acids or derivatives thereof are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

All publications and patents mentioned in the above specification are herein incorporated by reference. Various modifications and variations of the described compounds, compositions, methods and uses of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical, biological and chemical sciences are intended to be within the scope of the following claims.

EXAMPLES

Example 1

This example describes the extraction of oil from a wet material. A coagulum from krill comprising about 70% water, 15% lipids and about 15% other dry matter, mainly proteins, was obtained as described in WO/2009/027692, incorporated by reference herein in its entirety. This material was subjected to an extraction procedure as follows. 3500 grams of pure ethanol was added to 1004 grams of the coagulum and stirred for 45 minutes. The mixture was then filtered through a filter paper applying vacuum on the receiving flask to obtain 3854 gram of filtrate. 1179 gram of the filtrate was subjected to evaporation on a rotary evaporator and the obtained dry matter was washed 4 times with a 60% solution of ethanol and finally the solvent was evaporated in a rotary evaporator. The obtained oil, 23.7 gram, was solid at room temperature and comprised 76.8% phospholipids. Water is removed by freeze drying.

The content of EPA was 200 mg/gram and the content of DHA 87 mg/gram oil. The composition of the phospholipid fraction was as follows:

| Phospholipid | Weight-% | Mol-% | MW [g/mol] |
|---|---|---|---|
| PC | 71.97 | 93.03 | 790.0 |
| 1-LPC | 0.24 | 0.45 | 534.5 |
| 2-LPC | 0.73 | 1.39 | 534.5 |
| PI | —*) | —*) | 907.0 |
| LPI | —*) | —*) | 629.5 |
| PS-Na | —*) | —*) | 833.0 |
| LPS | —*) | —*) | 555.5 |
| SPH | —*) | —*) | 812.0 |
| PE | 3.37 | 4.47 | 770.0 |
| LPE | —*) | —*) | 492.5 |
| APE | —*) | —*) | 1032.0 |
| PG | —*) | —*) | 820.0 |
| DPG | —*) | —*) | 774.0 |
| PA | —*) | —*) | 746.0 |
| LPA | —*) | —*) | 468.5 |
| Other | 0.53 | 0.66 | 812.0 |
| Sum | 76.83 | 100.00 | |
| Phosphorus | 3.03 | | |

Example 2

This example describes an alternative method for extraction of oil from the krill wet material, starting from a frozen paste from krill, which was subjected to an extraction procedure as described below. Unlike example 1, all steps were performed under a nitrogen atmosphere.

The paste comprises about 65% water (assessed via dry matter), 17% lipids (about equal weights of phospholipids and neutral lipids), and about 18% other dry matter, mainly proteins. Within the lipids, the proportions of certain fatty acids by weight were as follows: C16:0 about 15-17%; C14:0 about 6-10%; C18:3 n-3 about 1.4-3.1%; and C18:4 n-3 about 3.5-7%.

100 kg of the frozen coagulum (−20° C.) was added to a vessel. Based on the water content of the coagulum, 350 kg of pure ethanol (99.8% w/w, room temp) was then added to the vessel, giving a final ethanol concentration in the liquid phase of about 84% w/w (~350 kg ethanol in 415 kg liquid solvents). Ethanol was added to give near to the desired final concentration, and then water content was checked by Karl Fischer titration and extra ethanol was added to give the correct final amount.

The mixture was stirred in the vessel for 45 minutes, with gentle heating if required. Four final temperatures were studied in separate batches, namely a) 2° C., b) 10° C., c) 15° C. and d) 20° C. After stirring was complete, the mixtures were allowed to settle, and they each included a red-coloured liquid phase and a wet slurry which contained shell fragments and other insoluble materials. To remove the liquid phase from the slurry the mixtures were decanted, and the liquid material was put through a coarse filter and then serial-filtered through a 75 μm and 5 μm cartridge filter to obtain a) 345 kg, b) 366 kg, c) 372 kg or d) 374 kg of filtrate, with residual material remaining in the filtration cake. Smaller cartridge filters (e.g. 1.2 μm) have also been used.

The filtrates were then subjected to a sequence of washes. Firstly, de-ionized water was added to give ~60% w/w ethanol solutions (a: 137 kg water; b: 149 kg; c: 152 kg; d: 155 kg) and the mixtures were stirred for 10-15 minutes and left to settle for 12-24 h at room temperature (15-20° C.) in vessels having a valve at the base. The bottom phase was isolated by draining the bottom phase through the valve, to give between 5.4-9.0 kg of a lipid-rich fraction. The lipid-rich fraction was re-washed 2 to 5 times with 60% w/w ethanol at room temperature to give a final material which contained about 80% by weight phospholipids and 20% neutral lipids. In even the first wash, 85% of TMAO was removed, and the further washes led to material with undetectable TMAO (less than 1 mgN/100 g i.e. at least 20-fold lower than reported in Table X of WO2013/102792).

This lipid-rich material was treated at least once by cold acetone precipitation. Three parts w/w acetone were added and the lipid rich material was dissolved by gentle heating and slow stirring. The stirring was stopped and the mixture was cooled to 4° C. for precipitation. When the precipitation was complete, the upper solvent phase was removed. This cold precipitation procedure was performed three times in total, after first re-dissolving in fresh acetone each time.

The precipitate was then subjected to evaporation and freeze-drying to remove residual acetone and water. Batch c (i.e. extracted at 15° C., then washed 3×60% EtOH before cold acetone precipitation) provided 1.9 kg of solid material (an orange wax) consisting of 98% phospholipids/1.7% neutral lipids with a water content of 3%. The content of EPA was 19.2 g/100 g and the content of DHA was 11.0 g/100 g solid material. The composition of the phospholipid fraction measured by $^{31}$P NMR was as follows:

| Phospholipid | Weight-% | Mol-% | MW [g/mol] |
|---|---|---|---|
| PC | 82.59 | 89.03 | 790.0 |
| 1-LPC | —*) | —*) | 534.5 |
| 2-LPC | 0.12 | 0.19 | 534.5 |
| PI | 0.47 | 0.44 | 907.0 |
| LPI | —*) | —*) | 629.5 |
| PS-Na | —*) | —*) | 833.0 |
| LPS | —*) | —*) | 555.5 |
| SPH | —*) | —*) | 812.0 |
| PE | 8.25 | 9.13 | 770.0 |
| LPE | —*) | —*) | 492.5 |
| APE | 0.59 | 0.49 | 1032.0 |
| PG | —*) | —*) | 820.0 |
| DPG | —*) | —*) | 774.0 |
| PA | —*) | —*) | 746.0 |
| LPA | —*) | —*) | 468.5 |
| Other | 0.69 | 0.73 | 812.0 |
| Sum | 92.72 | 100.00 | |
| Phosphorus | 3.64 | | |

*)= not observed, no signal assignment

Thus, based on total weight of the material analysed by NMR, nearly 93% of the final material was phospholipid. After compensating for residual water (about 3%), residual organic solvent, and salts/minerals present after ignition, the overall purity was 98%. Thus this process provides phospholipids with higher purity than seen using Example 1.

Further analysis of lipid composition was performed by HPLC, and results are shown below (grams per 100 g of oil):

| Parameter | Results |
|---|---|
| Lipid composition[1] | |
| Triacylglycerol | <0.5 |
| Diacylglycerol | <0.5 |
| Monoacylglycerol | <1 |
| Free fatty acids | <0.5 |

-continued

| Parameter | Results |
|---|---|
| Cholesterol | <0.5 |
| Cholesterol ester | <0.5 |
| Phosphatidylethanolamine | 7.7 |
| Phosphatidylinositol | <1 |
| Phosphatidylserine | <1 |
| Phosphatidylcholine | 92 |
| Lyso-phosphatidylcholine | <0.5 |
| Total polar lipids | 99.4 |
| Total neutral lipids | <0.5 |
| Total sum lipids | 99.6 |
| Fatty acid composition[(2)] | |
| Sum saturated fatty acids | 17.8 |
| Sum monoenic fatty acids | 9.1 |
| Sum PUFA (n-6) fatty acids | 1.2 |
| Sum PUFA (n-3) fatty acids | 34.4 |
| Sum total PUFA fatty acids | 35.8 |
| Sum fatty acids total | 62.7 |
| Cholesterol | 0.31 weight % |
| Astaxanthin/esters | <2 mg/kg |
| Water content | 3% |

Looking at specific fatty acids, proportions were as follows, measured across several batches:

| | C14:0 | C16:0 | 16/14 Ratio | C18:3 n-3 | C18:4 n-3 | 18:4/18:3 Ratio |
|---|---|---|---|---|---|---|
| Wet paste | 6-10% | 15-17% | 2-2.5 | 1.4-3.1% | 3.5-7% | 2-3 |
| Final material | 1.0-1.5% | 15-17% | 12-16 | 1.0-2.5% | 1.0-2.5% | 1-1.5 |

The purified phospholipids included both ether-linked and ester-linked fatty acids, but 10% or fewer were ether-linked NMR showed ether-linked fatty acid moieties at position sn1 but not at sn2, and ether-linked fatty acids were either fully saturated or were monounsaturated. Where a phospholipid was a phosphatidylcholine, about 10% of the molecules included ether-linked fatty acids; where a phospholipid was a phosphatidylethanolamine (with or without N-acetylation), about 40% of the molecules included ether-linked fatty acids. PUFAs were seen only with ester linkages. 30-40% by weight of fatty acids in the purified phospholipids were omega-3, and these were distributed at the sn1 and sn2 positions (mainly at sn2). Most of the omega-3 fatty acids were EPA and/or DHA, with about 2× more EPA than DHA.

The phosphatidylethanolamine content using this process was higher than seen when using the method of Example 1 (about 2× higher).

The lysophosphatidylcholine content (0.2-0.4 mol %) is very low in the purified phospholipids, when compared both to the amount observed using the method of Example 1 (about 1%) and in the starting wet material (about 1.2-1.4 mol %). No molecules were detected where fatty acid chains had been lost at both the sn1 and sn2 positions. Lyso-phosphatidylethanolamine (with or without N-acetylation) and lyso-phosphatidylinositol also were not seen.

Levels of astaxanthins were much lower in the purified phospholipids when compared to the material obtained in Example 1. This reduction was even visible due to the weaker red colour.

Amino acids, TMAO and homarine were all below LOQ by standard analytical methods.

Thus very pure krill phospholipids can be achieved by a process using extraction in 84% ethanol, followed by washing in 60% ethanol, and then multiple steps of cold-acetone precipitation.

Example 3

Rather than being subjected to cold acetone precipitation, the washed lipid-rich material produced during example 2 (80% phospholipid, 20% neutral lipid) was precipitated using ethyl acetate. In initial testing, the material was thoroughly mixed with 3 parts of ethyl acetate at room temperature and then placed at 4° C., −11° C. or −20° C. No precipitation was seen at 4° C., but there was some phase separation at −11° C. and precipitation was observed at −20° C.

Further washed lipid-rich material was mixed with 2, 3 or 5 parts of ethyl acetate and placed at −20° C. to achieve precipitation. With 3 parts of solvent the phospholipid yield was 32%, but with 5 parts of solvent the yield was 66%. Re-precipitation of this material gave results as follows:

| Precipitation | Yield | Phospholipid | Neutral lipid | Phospholipid yield |
|---|---|---|---|---|
| 1 | 65.6% | 96.1% | 3.9% | 81.6% |
| 2 | 95.4% | 99% | 1% | 62.6% |

Thus phospholipids can be effectively purified from the washed krill extract using repeated steps of precipitation with 5 volumes of EtOAc at −20° C.

Example 4

This example provides data on different formulations of krill phospholipid concentrates (prepared as described above) in combination with fish oil concentrates or ethyl esters. Krill phospholipid concentrates as a stock solution in ethanol were mixed with triglycerides EPAX 6015 Triglycerides (TG/N) containing 540 mg/g DHA and 140 mg/g EPA (as fatty acid). Ethanol was evaporated from the mixtures and then the viscosity, dispersion behavior, EPA/DHA content and ethanol content of the mixtures was determined. The following Table provides the composition of the mixtures. Additional additives were included in some of the formulations as indicated.

Sample Compositions (by Weight)

| Sample | Krill-PL (%) | Fish oil TG (%) | EtOH (%) | Other additives |
|---|---|---|---|---|
| TG-8 | 40. | 60.0 | 0.0 | |
| TG-9 | 39.3 | 58.9 | 1.8 | |
| TG-10 | 35.2 | 53.0 | 1.2 | MCT (%) 10.5 |
| TG-11 | 35.1 | 52.7 | 1.9 | GlycerylTrioctanoate (%) 10.3 |
| TG-12 | 35.7 | 53.2 | 1.1 | Lauric acid (%) 10.0 |
| TG-13 | 35.2 | 52.8 | 2.0 | Polysorbate 20 (%) 10.1 |
| TG-14 | 35.4 | 52.7 | 1.9 | Polysorbate 80 (%) 10.0 |
| TG-15 | 31.3 | 46.9 | 1.7 | Propylene glycol (%) 20.0 |

The following Table provides data on the viscosity of the different formulations at various temperatures.

Viscosity (Measured on Anton Paar Lovis 2000M Falling Sphere Viscometer)

| Sample | 25° C. (mPas) | 30° C. (mPas) | 35° C. (mPas) | Observations |
|---|---|---|---|---|
| TG-8 | n.d. | n.d. | n.d. | Semisolid |
| TG-9 | 120 | 95.72 | 77.25 | |
| TG-10 | 120.6 | 95.72 | 77.93 | |
| TG-11 | 82.99 | 67.78 | 56.8 | |
| TG-12 | 109.1 | 87.59 | 70.87 | |
| TG-13 | 128.8 | 101.5 | 81.74 | |
| TG-14 | 137.2 | 108.6 | 87.77 | |
| TG-15 | n.d | n.d | n.d. | Phase separation |
| Superba | 1600 | | | |

The following Table provides the calculated EPA and DHA content of the formulations by mass.

Calculated Theoretical EPA/DHA Content

| Sample | EPA (mg/g) | DHA (mg/g) |
|---|---|---|
| TG-8 | 389.9 | 119.2 |
| TG-9 | 381.6 | 116.6 |
| TG-10 | 343.4 | 104.9 |
| TG-11 | 341.5 | 104.4 |
| TG-12 | 345.0 | 105.5 |
| TG-13 | 342.0 | 104.5 |
| TG-14 | 342.1 | 104.6 |
| TG-15 | 304.1 | 92.9 |
| Superba | 128 | 64 |

The TG-10-12, TG-13, and TG-14 formulations were evaluated in dispersion behavior tests. 1 mL of the formulations was were dispersed in 250 ml simulated gastric fluid without pepsin. The dispersions were stirred at 60 rpm for 5 hours at 37° C. For formulation TG 10, TG 11, TG 13 and TG 14 a turbid dispersion was observed after 5 h stirring. Formulation TG 12 resulted in a clear solution with the lipid phase swimming on the surface. Superba gave a coarse dispersion in the aqueous phase with large visible droplets on the surface. For formulation TG 13 and TG 14 most of the TG fraction was dispersed finely and almost fully in the aqueous phase as fine droplets. For formulation TG 10 and TG 11 phase separation could be observed after end of stirring. Hence formulation TG-13 and TG-14 performed best in the dispersion test.

The data above shows that inclusion of 2% ethanol and 10% polysorbates in a formulation of 40:60 krill phospholipid concentrate:fish oil triglyceride concentrate greatly improves viscosity and dispersion. The observed dispersion characteristics with addition of polysorbate was superior to that observed for krill oil.

The invention claimed is:

1. A lipid formulation comprising:
about 25 to 55% w/w of a krill oil phospholipid fraction comprising a mixture of phospholipid compounds of formula (I):

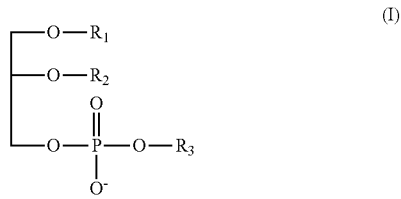

wherein:
R1 and R2 are each independently selected from a fatty acid moiety of formula COCnHm, a fatty acid moiety of formula $CH_2C_nH_m$, and H;
R1 and R2 include omega-3 fatty acid moieties, such that at least 30% by weight of the phospholipid compounds is composed of omega-3 fatty acid moieties;
at least 90% by weight of total omega-3 fatty acid moieties are at position $R_2$;
$R_1$ and $R_2$ are not both H in a phospholipid compound;
$R_3$ is selected from H, a choline moiety, an ethanolamine moiety, a N acetylethanolamine moiety, an inositol moiety, and a serine moiety; and
$R_3$ is a choline moiety in at least 85% by number of the compounds of formula (I);
about 40% to 70% w/w of a fish oil triglyceride omega-3 concentrate comprising a combined content of EPA and DHA of from about 45% to 80% w/w of said triglyceride omega-3 concentrate so that the lipid formulation comprises a total EPA and DHA content of from about 350 mg to 700 mg per gram of said formulation;
1% to 3% w/w of ethanol and 5% to 15% w/w of a surfactant selected from the group consisting of a polysorbate and a sorbitan ester, wherein said polysorbate is selected from the group consisting of Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), and Polysorbate 80 (Polyoxyethylene (20) sorbitan monooleate) and wherein said sorbitan ester is selected from the group consisting of Sorbitan monolaurate, Sorbitan monopalmitate, Sorbitan monostearate, Sorbitan monooleate, Sorbitan sesquioleate, Sorbitan trioleate and Sorbitan isostearate.

2. The lipid formulation of claim 1, wherein said fish oil triglyceride omega-3 concentrate is characterized in comprising a combined content of EPA and DHA of from about 60% to 80% w/w of said triglyceride omega-3 concentrate.

3. The lipid formulation of claim 1, wherein said lipid formulation comprises a total EPA and DHA content of from about 400 mg to 600 mg per gram of said formulation.

4. The lipid formulation of claim 1, wherein said lipid formulation comprises a total EPA and DHA content of from about 425 mg to 575 mg per gram of said formulation.

5. The lipid formulation of claim 1, wherein said lipid formulation has a viscosity of from about 20 to 200 mPas at 30° C.

6. The lipid formulation of claim 1, wherein said lipid formulation has a viscosity of from about 50 to 150 mPas at 30° C.

7. The lipid formulation of claim 1, wherein said formulation is provided in a formulation selected from the group consisting of a capsule, a tablet, a liquid, a powder, an emulsion, a dietary supplement, a nutritional supplement, a beverage and a functional food.

* * * * *